(12) United States Patent
Mett et al.

(10) Patent No.: US 9,778,220 B2
(45) Date of Patent: Oct. 3, 2017

(54) ELECTROCHEMICAL GAS SENSOR

(71) Applicant: Dräger Safety AG & Co. KGaA, Lübeck (DE)

(72) Inventors: Frank Mett, Lübeck (DE); Sabrina Sommer, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 289 days.

(21) Appl. No.: 14/627,120

(22) Filed: Feb. 20, 2015

(65) Prior Publication Data

US 2015/0241382 A1   Aug. 27, 2015

(30) Foreign Application Priority Data

Feb. 21, 2014   (DE) ...................... 10 2014 002 502

(51) Int. Cl.
*G01N 27/28* (2006.01)
*G01N 27/30* (2006.01)
*G01N 27/404* (2006.01)

(52) U.S. Cl.
CPC ................................ *G01N 27/4045* (2013.01)

(58) Field of Classification Search
CPC .. G01N 27/4045; G01N 27/28; G01N 27/283; G01N 27/30; G01N 27/302; G01N 27/3014; G01N 27/304; G01N 27/40; G01N 27/403; G01N 27/4166
See application file for complete search history.

(56) References Cited

U.S. PATENT DOCUMENTS

| 4,406,770 | A | * | 9/1983 | Chan .................. G01N 27/4045 204/406 |
| --- | --- | --- | --- | --- |
| 5,076,904 | A | | 12/1991 | Kiesele et al. |
| 5,234,567 | A | | 8/1993 | Hobbs et al. |
| 5,331,310 | A | | 7/1994 | Stetter et al. |
| 6,098,523 | A | | 8/2000 | Warburton |
| 6,248,224 | B1 | | 6/2001 | Kitzelmann |
| 2002/0033334 | A1 | * | 3/2002 | Tschuncky ............. G01N 27/40 204/415 |
| 2003/0038029 | A1 | * | 2/2003 | Davis ................. G01N 27/4045 204/400 |
| 2010/0170795 | A1 | * | 7/2010 | Cowburn ............. G01N 27/404 204/406 |
| 2011/0226619 | A1 | * | 9/2011 | Eckhardt .............. G01N 27/401 204/417 |

FOREIGN PATENT DOCUMENTS

| EP | 0 395 927 B1 | 1/1993 |
| --- | --- | --- |
| EP | 0 556 558 B1 | 4/2002 |

* cited by examiner

*Primary Examiner* — Susan D Leong
(74) *Attorney, Agent, or Firm* — McGlew and Tuttle, P.C.

(57) ABSTRACT

An electrochemical gas sensor (10) with a housing (11), with an electrolyte reservoir (12) and with a plurality of electrodes (31, 32, 33). The electrodes (31, 32, 33) include at least one working electrode (31), one counterelectrode (32) and one reference electrode (33). The electrolyte reservoir (12) is filled with a liquid electrolyte (60). All of the electrodes (31, 32, 33) are arranged at or on a common electrode carrier (20).

10 Claims, 2 Drawing Sheets

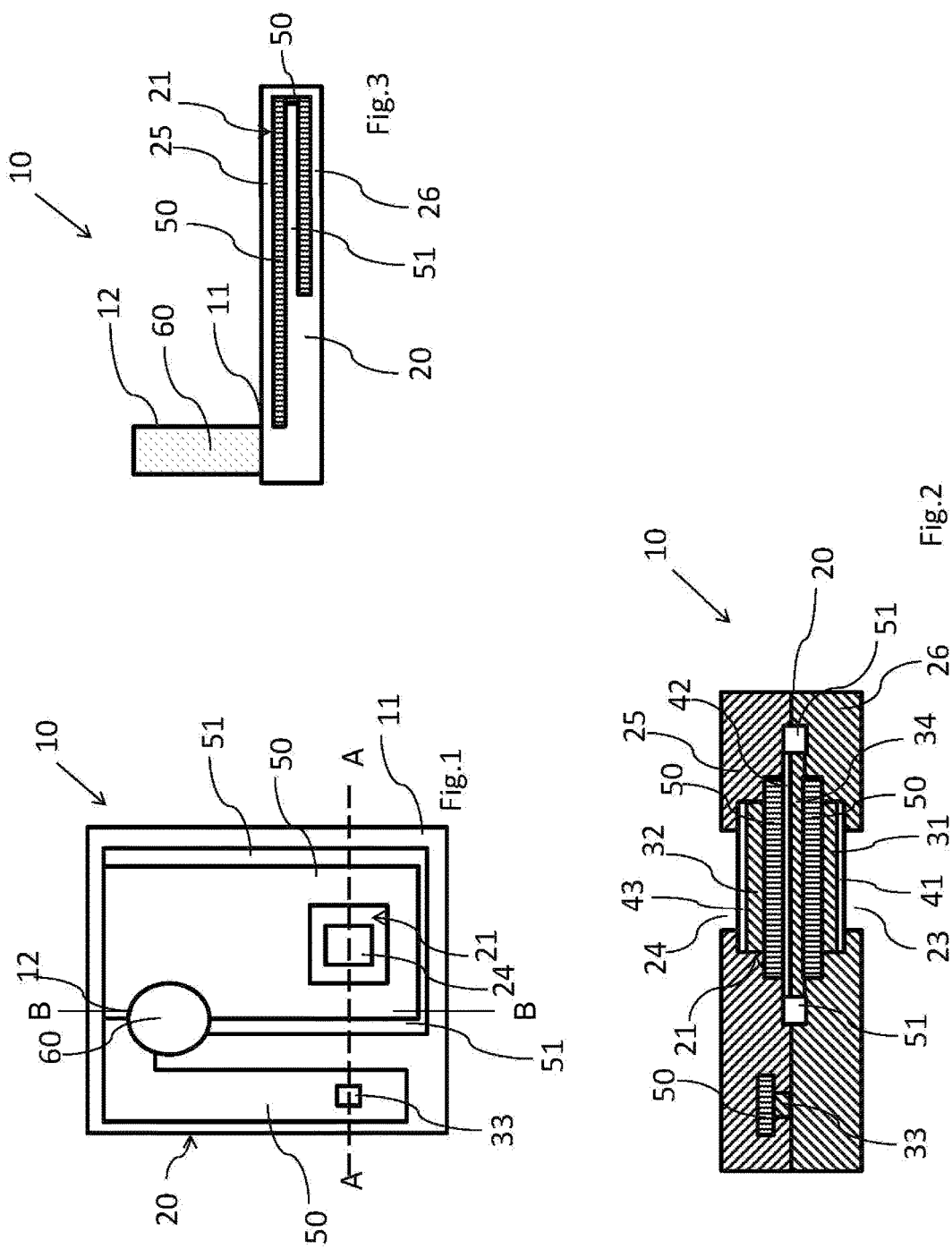

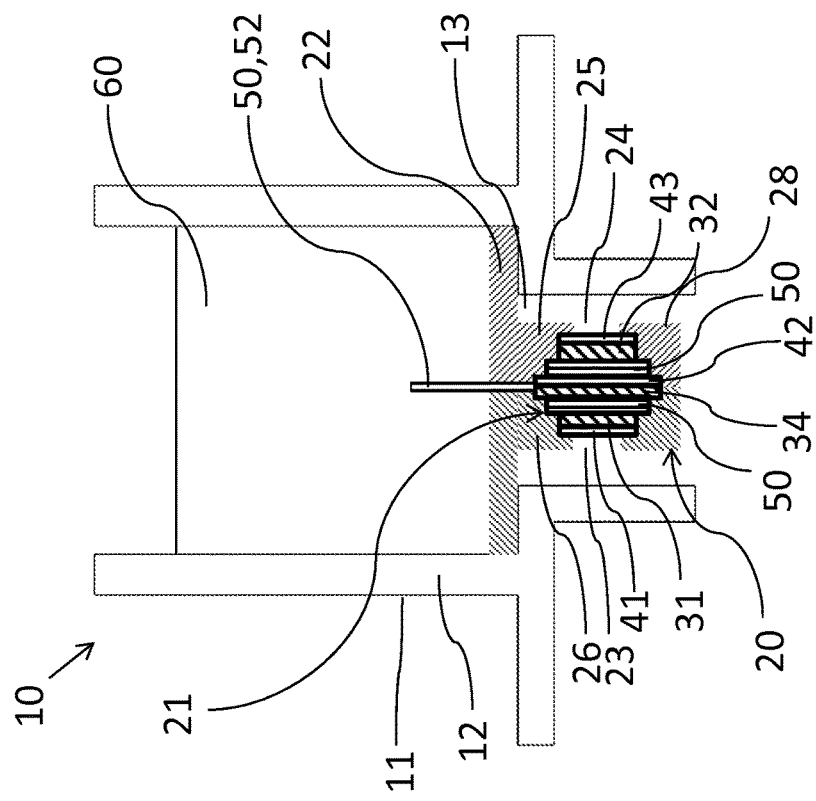
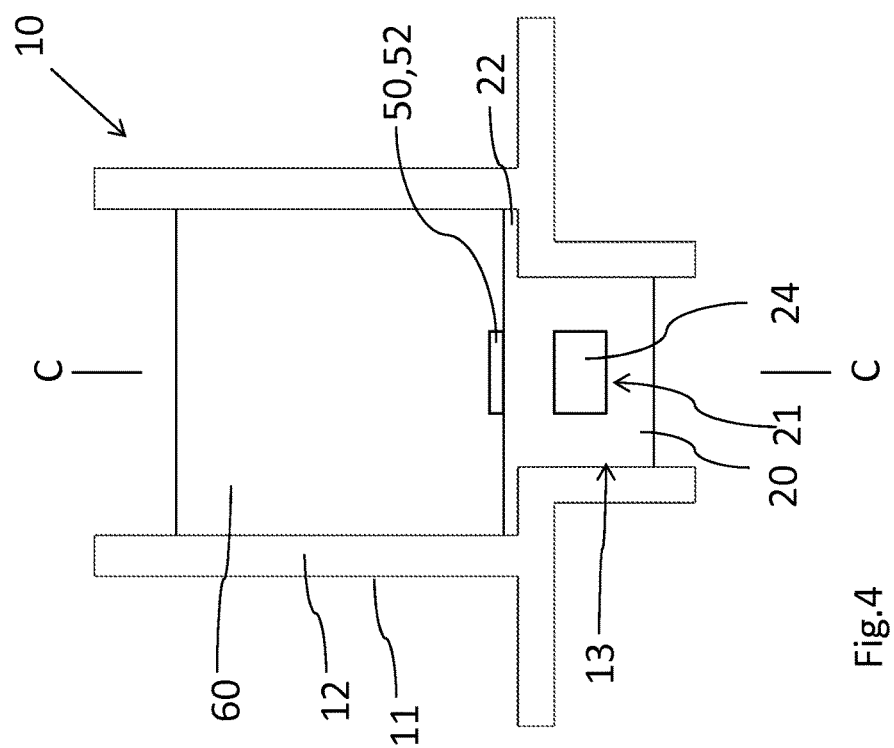

ELECTROCHEMICAL GAS SENSOR

CROSS REFERENCE TO RELATED APPLICATIONS

This application claims the benefit of priority under 35 U.S.C. §119 of German Patent Application DE 10 2014 002 502.0 filed Feb. 21, 2014, the entire contents of which are incorporated herein by reference.

FIELD OF THE INVENTION

The present invention especially to an electrochemical gas sensor gas sensor with a housing, with an electrolyte reservoir and with a plurality of electrodes, wherein the electrodes comprise at least one working electrode, one counterelectrode and one reference electrode and wherein the electrolyte reservoir is filled with a liquid electrolyte, particularly that can be used to detect $NH_3$ and/or $NH_3$-containing gas mixtures.

BACKGROUND OF THE INVENTION

Electrochemical gas sensors are generally known. They usually have a plurality of electrodes, which are in conductive contact with an electrolyte liquid and form a galvanic element, hereinafter also called electrochemical measuring cell, in this manner. There are both sensors that are used stationarily and sensors that are used in portable devices. It is desirable, especially in case of stationary sensors, that they be constantly able to function over the longest possible period of time and be tolerant to fluctuations in the measuring range.

The technical field of use, especially for sensors with which nitrogen-hydrogen compounds can be detected, ranges, for example, from the chemical industry to agricultural plants over the monitoring of refrigerating plants. The sensors are used especially to recognize critical concentrations of flammable and/or toxic gases and to warn against a corresponding risk. The monitoring of the concentrations of ammonia ($NH_3$), hydrazine and amines is of interest, in particular.

For example, EP 0 395 927 B1 discloses in this connection an electrochemical measuring cell for determining ammonia or hydrazine in a gaseous and liquid test sample, with at least one measuring electrode and a counterelectrode. To generate a reference potential for the determination of ammonia or hydrazine, a reference electrode, whose potential is used as a reference point for the measurement, is introduced into this measuring cell. EP 0 556 558 B1 also discloses such an electrochemical measuring cell for determining ammonia, amines, hydrazine and hydrazine derivatives.

The detection of the nitrogen-hydrogen-containing compounds, e.g., ammonia, various amines or hydrazine, typically takes place in such measuring cells by means of a corresponding reaction between the gas flowing into the sensor, the electrodes and the electrolyte of the sensor.

However, various problems may arise in such prior-art electrochemical measuring cells. For example, protons released at the working electrode may lead to a lowering of the pH value at the electrode. It may happen in such a case that more ammonia is oxidized only when the protons have been successfully neutralized. It may thus happen after a certain time of continuous gas admission that the measured signal drops (collapses) despite constant gas concentration.

SUMMARY OF THE INVENTION

Based on this, an object of the present invention is to overcome these and other drawbacks of the state of the art and to provide an improved electrochemical gas sensor. In particular, a gas sensor shall be provided, which has the highest measuring accuracy possible and has the best possible signal stability during continuous load. Furthermore, the gas sensor shall be able to be manufactured at the lowest possible cost and in the simplest possible manner.

According to the invention, an electrochemical gas sensor is provided comprising a housing, an electrolyte reservoir filled with a liquid electrolyte and a plurality of electrodes comprising at least one working electrode, at least one counterelectrode and at least one reference electrode. The electrochemical gas sensor further comprises a common electrode carrier, wherein all of the electrodes are arranged at or on the common electrode carrier.

According to a further aspect of the invention a method for gas sensing with an electrochemical gas sensor is provided. The method comprises the steps of providing an electrochemical gas sensor comprising a housing, an electrolyte reservoir filled with a liquid electrolyte, a plurality of electrodes comprising at least one working electrode, at least one counterelectrode and at least one reference electrode and a common electrode carrier, wherein all of the electrodes are arranged at or on the common electrode carrier, exposing the electrochemical gas sensor to a gas and detecting one or more compounds in the gas. Advantageously, $NH_3$ and/or $NH_3$-containing gas mixtures in the gas are detected.

In such an electrochemical gas sensor with a housing, with an electrolyte reservoir and with a plurality of electrodes, wherein the electrodes comprise at least one working electrode, one counterelectrode and one reference electrode and wherein the electrolyte reservoir is filled with a liquid electrolyte, provisions are made by the present invention for all of the electrodes to be arranged on the common electrode carrier.

The housing preferably has a gas inlet and a gas outlet. The gas to be tested, for example, the ambient air, can enter in this manner the gas sensor and react with the working electrode. For example, the ammonia contained in the ambient air can be oxidized in such a gas sensor by means of the electrolyte present in the electrolyte reservoir at the working electrode. The ammonium ions formed in the process can then diffuse to the counterelectrode and be deprotonated there. The ammonia formed in turn in the process can then leave the sensor through the gas outlet. The reaction at the working electrode leads to a detectable current flow in the galvanic cell. The current flow thus indicates the presence of the gas to be detected. It is, of course, also possible in this connection that another nitrogen-hydrogen-containing gas can be detected by means of the gas sensor depending on the electrolyte and the electrode material selected.

The electrode carrier thus represents a holder, at or on which both the working electrode and the counterelectrode and the reference electrode of the gas sensor are arranged. The electrode carrier is thus a common holder for the electrodes of the gas sensor. It is advantageous if the electrode carrier consists of an electrically nonconductive material.

Each of the electrodes may have a two-dimensional (flat) shape. All electrodes are preferably of a flat design. For example, they may be each a membrane, which is coated with metal, carbon or a mixture of metal and carbon. The membrane is preferably permeable to gases and/or inert to the gas to be detected as well as to the electrolyte. The membrane may be simply a film made of metal or carbon or a sheet made of the corresponding electrode material. The flat electrodes may be applied, for example, to the surface of the electrode carrier. The electrode carrier itself may likewise be of a flat design or have at least one section having a flat design. The common holder may be both that the electrodes are arranged next to each other on or at the surface of the electrode carrier and also that the electrodes are arranged stacked one on top of another on or at the surface of the electrode carrier. A protective and/or separating layer may also be formed between the electrodes and the surface. Such a protective and/or separating layer may also be provided between the electrodes.

It is advantageous in any case if the electrode carrier has at least one first recess. This first recess may form, for example, the gas inlet of the gas sensor. The first recess may be formed opposite the working electrode. The working electrode, which has, as was described above, a flat design, can cover the recess in this manner. The gas flowing in through the gas inlet can then come directly into contact with the working electrode and react there correspondingly. For protection of the working electrode from contaminants, for example, dust deposits or the like, it is favorable if a gas-permeable membrane is arranged between the working electrode and the first recess.

It is recognized, furthermore, that it is advantageous if the electrode carrier has a second recess. This second recess may form the gas outlet of the gas sensor. The second recess may be formed opposite the counterelectrode. The flat counterelectrode can cover the second recess in this manner. The gas formed at the counterelectrode can thus easily leave the gas sensor. It is likewise favorable in this case for the protection of the counterelectrode if a gas-permeable membrane is arranged between the second recess and the counterelectrode.

In a preferred embodiment, the electrode carrier forms a reaction chamber. The electrodes are arranged according to the present invention in this reaction chamber. The electrode carrier may form the wall of the reaction chamber. The reaction chamber represents the electrochemical cell of the gas sensor, in which the desired detection reaction takes place. This chamber is connected with the electrolyte reservoir via at least one electrolyte line. The electrolyte can be sent from the electrolyte reservoir to the electrodes by means of the electrolyte line.

It is also favorable if the electrode carrier forms a section of the housing of the gas sensor. The reaction chamber of the electrode carrier especially preferably forms a section of the housing of the gas sensor. The electrode carrier may also have an inner surface and an outer surface. The inner surface may be the surface at or on which the electrodes are arranged, as was described above. The outer surface can then form a section of the outer housing wall of the gas sensor. For example, the housing may have a mount for the electrode carrier. The housing is preferably open outwardly in the area of the mount. In other words, the mount forms an opening in the housing of the gas sensor. This opening can be closed by inserting the electrode carrier into the mount. The electrode carrier preferably has a fastening section in this case. The electrode carrier can be fixed in the mount with this fastening section.

The mount may form at the same time a limitation of the electrolyte reservoir. The electrolyte reservoir can be able to be closed by the electrode carrier in this manner, because when, as was described above, the electrode carrier is inserted into the mount, the opening, which forms the limitation of the electrolyte reservoir, is closed. It is preferred in this connection if the electrode carrier is inserted into the mount such that the reaction chamber is arranged outside the electrolyte reservoir. The reaction chamber especially preferably now forms a section of the outer housing wall of the housing.

It is thus recognized that it is favorable if the electrode carrier has a reaction chamber and a fastening section. It is recognized, furthermore, that the electrode carrier may be arranged at least partially outside the electrolyte reservoir. In particular, it is preferred in this connection if the reaction chamber, especially preferably the electrodes, are arranged outside the electrolyte reservoir. On the one hand, the working electrode can be brought properly into contact with the ambient air flowing in this manner, and, on the other hand, gas flowing out can flow easily away from the counterelectrode. As was described above, an electrolyte line may be present between the electrolyte reservoir and the electrode section. Such an electrolyte line ensures that the electrodes arranged in the electrode section are always sufficiently surrounded by electrolyte, so that the desired reaction can take place between the electrodes and the gas to be detected.

The working electrode and the counterelectrode are stacked one on top of another in a sandwich-like pattern in a preferred embodiment of the gas sensor. It is preferred in this case if the working electrode and the counterelectrode are arranged concentrically in the mounted state of the electrode carrier. The electrodes can be arranged at very closely spaced locations from one another in this manner.

To achieve such an arrangement by means of the electrode carrier according to the present invention, it is favorable if the reaction chamber of the electrode carrier has a first wall section and a second wall section. Both the first wall section and the second wall section preferably have an outer surface and an inner surface. The inner surface is the surface facing the reaction chamber. The first and second wall sections are located opposite each other in the mounted state of the gas sensor such that the inner surfaces of the wall sections face each other. As was described above, the electrodes may be arranged at or on this inner surface. It is advantageous in this connection if the electrodes are arranged between the first wall section and the second wall section. In particular, the electrodes may now be arranged between the inner surface of the first wall section and the inner surface of the second wall section. The first recess of the electrode carrier, i.e., the gas inlet, may be formed in the first wall section. The second recess of the electrode carrier, i.e., the gas outlet, may be formed in the second wall section. It is favorable in this connection if the area of the first recess is smaller than the area of the second recess. Furthermore, it is advantageous if the area of the working electrode is smaller than the area of the counterelectrode. In this connection, the flat working electrode may lie on the first wall section and the flat counterelectrode lies on the second wall section, with the working electrode covering the first recess and the counterelectrode covering the second recess.

According to another embodiment, the first recess and the second recess are formed in the same wall section. It is advantageous in this case as well if the working electrode covers the first recess and the counterelectrode the second recess. The second wall section may act as a protective layer now, which covers both the working electrode and the counterelectrode.

Provisions may be made in an especially preferred embodiment for the counterelectrode and/or the working electrode to be covered by a separating layer. The separating layer, which covers the working electrode, may be the same separating layer that also covers the counterelectrode. The reaction chamber may consequently have a sandwich-like design in a very simple form such that the working electrode lies on the first wall section, the separating layer lies on the working electrode, the counterelectrode lies on the separating layer, and the second wall section lies on the counterelectrode. Of course a protective membrane each may be formed between the working electrode and the first wall section and/or between the counterelectrode and the second wall section. In any case, the separating layer may prevent a direct contact between the working electrode and the counterelectrode. It is advantageous in this connection if the separating layer can be impregnated with the electrolyte. The electrolyte can be guided in this manner from the electrolyte reservoir to the electrodes by means of the separating layer. The separating layer therefore extends preferably beyond the reaction chamber to the electrolyte reservoir. It can have in this manner a wick effect, by which the electrolyte is transported to the electrodes. The separating layer consequently has a wick effect. In other words, it is recognized that the separating layer may form an electrolyte line (transport conduit) between the electrolyte reservoir and the electrodes. To keep the distance over which the electrolyte is transported by means of the wick effect of the separating layer as short as possible, the electrolyte channels may be formed in the separating layer. For example, the electrolyte channels may be formed laterally in parallel to the electrodes covered by the separating layer. The electrolyte channels may also be formed laterally in parallel by the separating layer.

In a special embodiment of the gas sensor, the electrode carrier may be designed as a stamping-and-bending part or the like. It is advantageous in this connection if the first wall section and the second wall section are connected with one another by a predetermined kinking site. The electrode carrier can then be able to be kinked in the course of the assembly and/or manufacture such that the first wall section will come to lie on the second wall section on kinking the electrode carrier. The working electrode may be arranged on the first wall section in this case, while the counterelectrode may be arranged on the second wall section. The working electrode and the counterelectrode are preferably aligned here such that the working electrode will come to lie on the counterelectrode on kinking the electrode carrier. It is recognized that it is favorable if the working electrode and the counterelectrode are covered by a separating layer here as well. In this connection, the separating layer, which covers the working electrode and the counterelectrode, may be folded such that a first section of the separating layer covers the working electrode and a second section of the separating layer covers the counterelectrode, and the first section of the separating layer is located opposite the second section of the separating layer in the folded state. As an alternative to a predetermined kinking site, a predetermined breaking point may, of course, be provided as well.

In any case, the reference electrode of the gas sensor is also arranged according to the present invention at or on the electrode carrier. For example, a reference electrode having a flat design may be arranged laterally from the working electrode and/or laterally from the counterelectrode at or on the inner surface of the electrode carrier. It is advantageous in this case if the reference electrode is embedded into the separating layer or is covered by the separating layer. Another electrolyte channel, through which electrolyte can be guided to the reference electrode, may thus be formed in the separating layer.

In all these embodiments the gas sensor may have, furthermore, a protective electrode. It is especially favorable in this connection if the protective electrode is arranged between the working electrode and the counterelectrode. The protective electrode can prevent, for example, excess gas, which was not reacted at the working electrode, from reaching the counterelectrode. In addition, the protective electrode prevents gas formed at the counterelectrode from diffusing back to the working electrode. It is advantageous in this connection if a diffusion-limiting membrane is arranged between the counterelectrode and the protective electrode. If the separation layer has such a design that a first section covers the working electrode and a second section the counterelectrode, it is favorable if the protective electrode is arranged between the first and second sections of the separating layer. It is also meaningful in this connection if the diffusion-limiting membrane is arranged between the first and second sections of the separating layer.

The reaction chamber is preferably designed in this case as follows: A first wall section of the electrode carrier forms a first outer limitation of the reaction chamber. The first recess, which forms the gas inlet, is formed in this wall section. A protective membrane, which covers the first recess, lies on this first wall section. The working electrode having a flat design lies on the protective membrane. The working electrode is covered by the first section of the separating layer or a first separating layer. The protective electrode lies on this first section of the separating layer or on this first separating layer. The protective electrode is covered by the diffusion-limiting membrane. The second section of the separating layer or a second separating layer lies on the diffusion-limiting membrane. The counterelectrode lies on this second section of the separating layer or on this second separating layer. The counterelectrode is covered, in turn, by a protective membrane. The second wall section of the electrode carrier lies on this protective membrane. The second recess, which forms the gas outlet, is formed in this second wall section. The second wall section lies on the protective membrane such that the second recess lies completely over the counterelectrode. The area of the counterelectrode is preferably larger in this arrangement than the area of the working electrode. The area of the second recess is also larger than the area of the working electrode. The area of the second recess is also larger than the area of the first recess. The gas formed at the counterelectrode can diffuse in this manner rapidly and effectively. Furthermore, it is favorable in such an arrangement if the working electrode, the counterelectrode and the protective electrode are arranged concentrically in relation to one another in the mounted state of the electrode carrier. The area of the protective area is preferably larger than the area of the working electrode and especially preferably larger than the area of the counterelectrode. The protective electrode forms in this manner an effective barrier between the working electrode and the counterelectrode. It is therefore recognized that it is especially favorable if the area of the protective electrode is larger than the area of the working electrode and larger than the area of the counterelectrode.

It is advantageous in all these embodiments if the electrolyte is, for example, a system consisting of propylene carbonate, an ionic liquid and an organic mediator. Ethylene carbonate may be added as an additional component. For example, the propylene carbonate vapor pressure can be reduced in this manner. Protons can then be released at the working electrode, for example, for oxidizing $NH_3$. The pH value decreases there as a result. In return, the pH value increases at the counterelectrode due to the opposing reaction taking place there. The organic mediator may bring about a rapid pH compensation between the working electrode and the counterelectrode. The organic mediator may be preferably a quinoid compound. Especially nitrogen-hydrogen-containing compounds, such as ammonia, amines, hydrazine and hydrazine derivatives can be detected especially well in such a case. It is thus recognized that it is advantageous if the electrolyte contains a quinoid mediator.

Furthermore, the present invention makes provisions for the use of a gas sensor according to the present invention, preferably of a gas sensor according to one of the above-described embodiment variants, for detecting $NH_3$ and/or $NH_3$-containing gas mixtures.

Further features, specifics and details appear from the figures and exemplary embodiments described below. It is apparent that these exemplary embodiments are merely exemplary and that the person skilled in the art will arrive at further variants and exemplary embodiments without problems on the basis of the present description. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic top view of a gas sensor according to the present invention, wherein the top side of the gas sensor housing is transparent for the schematic illustration of the components arranged in the housing;

FIG. 2 is a cross sectional view through the gas sensor shown in FIG. 1, the section being taken along line A-A in FIG. 1;

FIG. 3 is a cross sectional view through the gas sensor shown in FIG. 1, the section being taken along line B-B in FIG. 1;

FIG. 4 is a side sectional view showing another exemplary embodiment for a gas sensor according to the present invention; and FIG. 5 is a view, rotated by 90°, of the exemplary embodiment shown in FIG. 4 in a cross section taken along line C-C in FIG. 4.

DESCRIPTION OF THE PREFERRED EMBODIMENTS

Referring to the drawings, the gas sensor 10 shown in FIGS. 1 through 5 has a housing 11, which is formed by an electrolyte reservoir 12 and an electrode carrier 20. The part of the housing 11 facing the viewer is shown as a transparent part, especially in the area of the electrode carrier 20, in order to show how the arrangement of the components described below in the interior of the electrode carrier 20 can be designed. It is apparent that FIG. 1 should be considered only as a representation of a basic, schematic design.

In any case, a liquid electrolyte 60 is present in the electrolyte reservoir 12. The electrode carrier 20 has a reaction chamber 21. Gas can enter the reaction chamber 21 through a first recess 23 (recognizable, for example, in FIG. 2) and exit through a second recess 24. The first recess 23 is formed on the underside of the electrode carrier 20 (cf. FIG. 2) in the example being shown, while the second recess 24 is formed in the opposite top side of the electrode carrier 20.

It is apparent that it is also possible, as an alternative, that the first recess 23 is formed in the top side and the second recess 24 in the underside of the electrode carrier 20. It is therefore recognized that the electrode carrier 20 has at least one first recess 23.

The reaction chamber 21 is connected with the electrolyte reservoir 12 via a separating layer 50. The separating layer 50 can guide the liquid electrolyte 60 present in the electrolyte reservoir 12 to the reaction chamber 21. The reaction chamber 21 is therefore in fluid connection with the electrolyte reservoir 12. The reaction chamber 21 and the separating layer 50 are enclosed, as can be recognized in FIGS. 2 and 3, by a first wall section 25 and a second wall section 26 of the electrode carrier. To further improve the feeding of the electrolyte 60, electrolyte channels 51 are formed laterally from the separating layer 50. These support the transport of the electrolyte from the electrolyte reservoir 12 to the reaction chamber 21. Two electrolyte channels 51 are present in the example being shown. It is, of course, also possible that only one electrolyte channel 51 is formed or that more than two electrolyte channels 51 are present.

Both the gas sensor 10 shown in FIGS. 1 through 3 and the gas sensor 10 shown as an example in FIGS. 4 and 5 has each a working electrode 31, a counterelectrode 32 and a protective electrode 34 arranged between the working electrode and the counterelectrode 32. The working electrode 31, the counterelectrode 32 and the protective electrode 34 are arranged in the reaction chamber 21. It is recognized, besides, in FIG. 2 and FIG. 5 that the electrodes 31, 32, 34 are arranged in a sandwich-like pattern.

It is recognized, furthermore, in FIGS. 1 and 2 that the gas sensor 10 may have, besides, a reference electrode 33. A gas sensor 10 corresponding to FIGS. 4 and 5 may also have such a reference electrode 33. The reference electrode 33 is likewise connected with the electrolyte reservoir 12 via the separating layer 50. As can be seen, moreover, in FIG. 2, the reference electrode 33 is covered by the separating layer in the example being shown. However, in a variant, which is not shown, the reference electrode 33 is embedded in the separating layer 50. In any case, the reference electrode 33 is also in fluid connection with the electrolyte reservoir 12, so that the electrolyte 60 is guided to the reference electrode 33 from the electrolyte reservoir 12 by means of the separating layer 50. It becomes clear from the top view in FIG. 1 and in the cross-sectional view in FIG. 2 that the reference electrode 33 is arranged at a laterally spaced location from the electrodes 31, 32, 34 arranged in the reaction chamber 21. However, all electrodes of the gas sensor 10 are in conductive contact with one another at the same time through the electrolyte 60.

A protective membrane 41 is arranged between the working electrode 31 and the first recess 23. The first recess 23 forms the gas inlet of the gas sensor 10. The protective membrane 41 prevents, for example, dust from the ambient air from being able to be deposited, causing disturbances, on the working electrode 31. The separating layer 50 is arranged over the working electrode 31. It is recognized that the separating layer 50 fully covers the working electrode 31. The protective electrode 34 is arranged over the separating layer 50. The protective electrode 34 is covered by a diffusion-limiting membrane 42. A further layer of the separating layer 50 is formed above the diffusion-limiting membrane 42. The counterelectrode 32 is arranged on this separating layer 50. The counterelectrode 32 is covered by a protective membrane 43. The protective membrane 43 forms a protective barrier between the counterelectrode 32 and the second recess 24, which forms the gas outlet of the gas sensor 10. The counterelectrode 31 and the working electrode 31 are covered by a separating layer 50 in this arrangement. The protective electrode 34 is designed in this arrangement of the electrodes 31, 32, 34 such that the area of the protective electrode 34 is larger than the area of the working electrode 31 and larger than the area of the counterelectrode 32.

It is recognized in both FIG. 2 and FIG. 3 as well as FIG. 5 that the reaction chamber 21 is defined by a first wall section 25 and a second wall section 26 of the electrode carrier 20. The electrode carrier 20 therefore forms the reaction chamber 12. The electrodes 31, 32, 34 are, in this case, arranged between the first wall section 25 and the second wall section 26. It is recognized, furthermore, that the reaction chamber 21 is connected with the ambient air via the first and second recesses 23, 24. The first recess 23 is smaller than the second recess 24. An electrolyte channel 51 each is formed laterally from the separating layers 50.

It is recognized, furthermore, in FIG. 3 that the electrode carrier 20 forms a section of the housing 11 of the gas sensor 10. The housing 11 comprises the wall of the electrolyte reservoir 12 and the wall of the electrode carrier 20. The separating layer 50 is arranged in the electrode carrier 20 such that it is in direct contact with the electrolyte 60 present in the electrolyte reservoir 12.

The separating layer 50, especially a section 52 of the separating layer 50 projecting from the electrode carrier 20, is in direct contact with the electrolyte 60 present in the electrolyte reservoir 12 in the alternative embodiment of the gas sensor 10 shown in FIGS. 4 and 5 as well. It is recognized here as well that the electrode carrier 20 forms a section of the housing 11. The electrode carrier 20 has a fastening section 22 here. The electrode carrier 20 is fixed with this fastening section 22 in a mount 13 of the electrolyte reservoir 12. The electrode carrier 20 is arranged here such that the part of the electrode carrier 20, in which the reaction chamber 21 is formed, forms a section of the housing 11. The electrode carrier 20 has an inner surface and an outer surface in this area. The inner surface defines the reaction chamber 21. The outer surface forms a section of the outer housing wall of the gas sensor 10.

All the features and advantages, including design details, three-dimensional arrangements and process steps appearing from the claims, the description and the drawings may be essential for the present invention both in themselves and in the many different combinations well.

For example, the electrolyte 60 is a composition comprised of solvent, conducting salt and a quinone compound in all examples shown. One example of such a composition is a mixture of a solvent, which contains 60 wt. % of propylene carbonate and 40 wt. % of ethylene carbonate, 0.1 mole of Hmin-FAP (1-hexyl-3-methylimidazolium-tris(pentafluoroethyl)-trifluorophosphate) and 0.5 mole of tert.-butyl hydroquinone. This composition may, of course, be varied, so that the ratio of propylene carbonate to ethylene carbonate is not limited by any means to a ratio of 60:40 weight percent. The molar quantity of the HMIM FAP and tert.-butyl hydroquinone is also variable.

While specific embodiments of the invention have been shown and described in detail to illustrate the application of the principles of the invention, it will be understood that the invention may be embodied otherwise without departing from such principles.

APPENDIX
List of Reference Numbers

| | |
|---|---|
| A | Line |
| B | Line |
| C | Line |
| 10 | Gas sensor |
| 11 | Housing |
| 12 | Electrolyte reservoir |
| 13 | Mount |
| 20 | Electrode carrier |
| 21 | Reaction chamber |
| 22 | Fastening section |
| 23 | Recess |
| 24 | Recess |
| 25 | Wall section |
| 26 | Wall section |
| 31 | Working electrode |
| 32 | Counterelectrode |
| 33 | Reference electrode |
| 34 | Protective electrode |
| 41 | Protective membrane |
| 42 | Membrane |
| 43 | Protective membrane |
| 50 | Separating layer |
| 51 | Electrolyte channel |
| 52 | Section |
| 60 | Electrolyte |

What is claimed is:

1. An electrochemical gas sensor comprising:
a housing having a gas inlet;
an electrolyte reservoir filled with a liquid electrolyte;
a plurality of electrodes comprising at least one working electrode, at least one counter electrode and at least one reference electrode; and
a common electrode carrier, wherein all of the electrodes are arranged at or on the common electrode carrier, the common electrode carrier includes parallel first and second wall sections with adjacent sides and opposite sides, the adjacent side of the first wall section lying against the adjacent side of the second wall section, the adjacent sides of the wall sections defining a reaction chamber, the working and counter electrodes being arranged in the reaction chamber, the opposite side of the first wall section defining a first recess forming part of the housing and the gas inlet, the opposite side of the second wall section defining a second recess forming part of the housing and a gas exit;
the electrolyte reservoir being mounted on the common electrode carrier and arranged laterally spaced from the plurality of electrodes and the first and second recesses with respect to a plane of the first and second wall sections.

2. An electrochemical gas sensor in accordance with claim 1, wherein the housing has a mount receiving the electrode carrier.

3. An electrochemical gas sensor in accordance with claim 1, further comprising a separating layer wherein the counter electrode and the working electrode are covered by the separating layer.

4. An electrochemical gas sensor in accordance with claim 3, wherein the separating layer forms an electrolyte conduit line between the electrolyte reservoir and the electrodes.

5. An electrochemical gas sensor in accordance with claim 3, wherein electrolyte channels are formed in the separating layer.

6. An electrochemical gas sensor in accordance with claim 3, wherein the reference electrode is embedded in the separating layer or is covered by the separating layer.

7. An electrochemical gas sensor in accordance with claim 1, wherein the gas sensor has, furthermore, a protective electrode.

8. An electrochemical gas sensor in accordance with claim 7, wherein an area of the protective electrode is larger than an area of the working electrode and larger than an area of the counter electrode.

9. An electrochemical gas sensor in accordance with claim 1, wherein the electrolyte contains a quinoid mediator.

10. An electrochemical gas sensor in accordance with claim 1, wherein the gas sensor is configured for detecting $NH_3$ and/or $NH_3$-containing gas mixtures.

* * * * *